United States Patent
Rawat et al.

(10) Patent No.: US 9,163,038 B2
(45) Date of Patent: Oct. 20, 2015

(54) PROCESS FOR SYNTHESIS OF CHIRAL 3-SUBSTITUTED TETRAHYDROQUINOLINE DERIVATIVES

(71) Applicant: Council of Scientific & Industrial Research, New Delhi (IN)

(72) Inventors: Varun Rawat, Pune (IN); Senthil Kumar Boopathi, Pune (IN); Arumugam Sudalai, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/385,976

(22) PCT Filed: Mar. 19, 2013

(86) PCT No.: PCT/IN2013/000178
§ 371 (c)(1),
(2) Date: Sep. 17, 2014

(87) PCT Pub. No.: WO2013/140419
PCT Pub. Date: Sep. 26, 2013

(65) Prior Publication Data
US 2015/0038714 A1    Feb. 5, 2015

(30) Foreign Application Priority Data
Mar. 19, 2012  (IN) .......................... 0797/DEL/2012

(51) Int. Cl.
| | |
|---|---|
| *C07F 7/02* | (2006.01) |
| *C07F 7/18* | (2006.01) |
| *C07D 215/20* | (2006.01) |
| *C07D 215/38* | (2006.01) |
| *C07D 471/06* | (2006.01) |
| *C07D 217/16* | (2006.01) |
| *C07D 217/22* | (2006.01) |
| *C07D 217/24* | (2006.01) |
| *C07D 491/056* | (2006.01) |

(52) U.S. Cl.
CPC ............ *C07F 7/1844* (2013.01); *C07D 215/20* (2013.01); *C07D 215/38* (2013.01); *C07D 217/16* (2013.01); *C07D 217/22* (2013.01); *C07D 217/24* (2013.01); *C07D 471/06* (2013.01); *C07D 491/056* (2013.01)

(58) Field of Classification Search
None
See application file for complete search history.

(56) References Cited

PUBLICATIONS

Jagdale et al., Asymmetric Synthesis of Tetrahydroquinolin-3-ols via CoCl2-Catalyzed Reductive Cyclization of Nitro Cyclic Sulfites with NaBH4, Org Lett (2009), 11(4):803-806.
Jagdale et al., A concise enantioselective synthesis of 1-[(S)-3-(dimethylamino)-3,4dihydro-6,7-dimethoxyquinolin-1(2H)-yl]propan-1-one, (S)-903, Tetrahedron: Asymmetry (2009), 20(3):335-339.
Di Fabio et al., Chiral tetrahydroquinoline derivatives as potent anti-hyperalgesic agents in animal models of sustained inflammation and chronic neuropathic pain, Bioorg Med Chem Lett (2007), 17(5):1176-1180.
Jia et al., Highly Enantioselective Synthesis of Polysubstituted Tetrahydroquinolines via Organocatalytic Michael/Aza-Henry Tandem Reactions, Org Lett (2011), 13(5):832-835.
Kang et al., Enantioselective Organocatalytic C—H Bond Functionalization via Tandem1,5-Hydride Transfer/Ring Closure: Asymmetric Synthesis of Tetrahydroquinolines, J Am Chem Soc (2010), 132(34):11847-11849.
Kotkar et al., Organocatalytic Sequential α-Amination-Horner-Wadsworth-Emmons Olefination of Aldehydes: Enantioselective Synthesis of γ-Amino-α, β-Unsaturated Esters, Org Lett (2007), 9(6):1001-1004.
Devalankar et al., Organocatalytic sequential α-aminoxylation and cis-Wittig olefination of aldehydes: synthesis of enantiopure γ-butenolides, Tetrahedron: Asymmetry (2012), 23(3-4):240-244.
Kumar et al., Organocatalytic Sequential α-Amination/Corey-Chaykovsky Reaction of Aldehydes: A High Yield Synthesis of 4-Hydroxypyrazolidine Derivatives, Org Lett (2012), 14(10):2468-2471.
Talluri et al., An organo-catalytic approach to the enantioselective synthesis of (R)-selegiline, Tetrahedron (2007), 63(39): 9758-9763.
Heier et al., An Asymmetric Synthesis of (R)-5-(Methylamino)-5,6-Dihydro-4H-Imidazo-[4,5,5-ij] Quinolin-2(1H)-One (1) and Its [2-14C]- and [6,7-3H2]-Labeled Forms, Journal of Labelled Compounds and Radiopharmaceuticals (1996), 38(12):1087-1098.
Gallou-Dagommer et al., Asymmetric Synthesis of Functionalized 1,2,3,4-Tetrahydroquinolines, Org Lett (2001), 3(13):2053-2056.

*Primary Examiner* — Heidi Reese
(74) *Attorney, Agent, or Firm* — Bret E. Field; Bozicevic, Field & Francis LLP

(57) ABSTRACT

The present invention relates to novel and concise process for the construction of chiral 3-substituted tetrahyroquinoline derivatives based on proline catalyzed asymmetric α-functionalization of aldehyde, followed by in situ reductive cyclization of nitro group under catalytic hydrogenation condition with high optical purities. Further the invention relates to conversion of derived chiral 3-substituted tetrahydroquinoline derivatives into therapeutic agents namely (−)-sumanirole (96% ee) and 1-[(S)-3-(di-methylamino)-3,4-dihydro-6,7-dimethoxy-quinolin-1(2H)-yl]propanone[(S)-903] (92% ee).

11 Claims, No Drawings

US 9,163,038 B2

PROCESS FOR SYNTHESIS OF CHIRAL 3-SUBSTITUTED TETRAHYDROQUINOLINE DERIVATIVES

TECHNICAL FIELD

The present invention relates to novel and concise process for the preparation of chiral 3-substituted tetrahydroquinoline derivatives based on proline catalyzed asymmetric α-functionalization of aldehyde, followed by in situ reductive cyclization of nitro group under catalytic hydrogenation condition with high optical purities.

Further, the invention relates to conversion of derived chiral 3-substituted tetrahydroquinoline derivatives into pharmacologically relevant therapeutic agents, namely (−)-sumanirole (96% ee) and 1-[(S)-3-(dimethylamino)-3,4-dihydro-6,7-dimethoxy-quinolin-1(2H)-yl]propa-none[(S)-903] (92% ee).

BACKGROUND AND PRIOR ART

Chiral substituted tetrahydroquinoline derivatives possess variety of pharmacological activities and hence, the current trend of research is looking for efficient methods for the construction of these derivatives. There is ample literature available on the construction of chiral tetrahydroquinoline derivatives. The 1,2,3,4-tetrahydroquinoline (THQ) is a very common structural motif found in numerous biologically active natural products and pharmacologically relevant therapeutic agents. For example, (−)-sumanirole [PNU-95666E, (1)] is a selective and high affinity agonist at the dopamine $D_2$ receptor subtype and has proven as a potential agent for the treatment of Parkinson's disease and restless leg syndrome. Also, 1-[(S)-3-(dimethylamino)-3,4-dihydro-6,7-dimethoxy quinolin-1(2H)-yl]propanone [(S)-903 (2)] has recently been identified as a potentially interesting positive inotropic agent, while (+)-duocarmycin D1 (3) has exhibited potent antitumor activity, whereas Anachelin H chromophore (3') has significant anti-bacterial activity (FIG. 1). Due to the significance of these scaffolds in drug discovery and medicinal chemistry, the development of new methodologies for the synthesis of 3-substituted THQs derivatives continue to be very active field of research in recent years.

FIG. 1. Structures of some THQ containing bioactive molecules

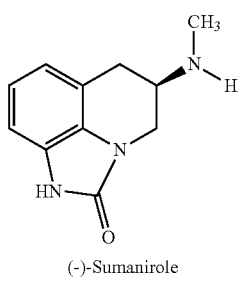

(−)-Sumanirole (1)

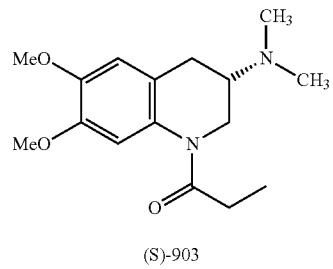

(S)-903 (2)

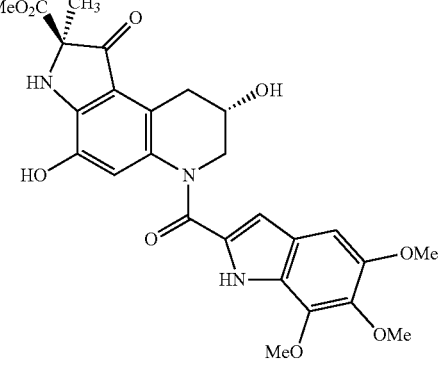

(+)-Duocarmycin D₁ (3)

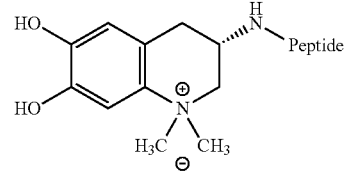

Anachelin H chromophore (3')

A few methods thus are reported in the literature for their synthesis. Rh-catalyzed reduction of chiral amino cinnamates by Isabelle Gallou-Dagommer et al. is reported in Org. Lett., 2001, 3 (13), pp 2053, whereas $CoCl_2$-catalyzed reductive cyclization of nitro cyclic sulfites is disclosed in Org. Lett., 2009, 11 (4), pp 803-806 by Arun R. Jagdale. Also Co-catalyzed concise enantioselective synthesis of 1-[(S)-3-(dimethylamino)-3,4-dihydro-6,7-dimethoxyquinolin-1(2H)yl] propan-1-one, (S)-903 is reported in Tetrahedron: Asymmetry 20, (3), 2009, PP 335-339.

Romano Di Fabio et al. in Bioorganic a Medicinal Chemistry Letters 17 (5), 2007, 1176-80 discloses the preparation of chiral tetrahydroquinoline derivatives by an asymmetric Mannich-type condensation reaction using commercially available vinyloxyethylsilane and a N-arylimino R-(+)-t-butyl lactate ester, in the presence of a catalytic amount of metal triflates as Lewis acids.

Highly enantioselective chiral bifunctional thiourea catalyzed asymmetric tandem reactions for synthesis of substituted tetrahydroquinolines in good yields and high enantioselectivities are demonstrated by Zhen-Xin Jia in Org. Lett., 2011, 13 (5), pp 832-835. Further Young Ku Kang et al in J. Am. Chem. Soc., 2010, 132 (34), pp 11847-11849 describes CSA (Camphorsulfonic acid) mediated efficient formation of ring-fused tetrahydroquinolines in high enantioselectivities.

However, the use of expensive chiral starting materials, multi-step reaction sequences, use of protection and deprotection of various functional groups and low overall yields are some of the limitations of the existing routes. In this regard, an organocatalytic protocol that provides for the efficient synthesis of chiral 3-substituted THQs is highly desirable.

In recent years, it has been proven that proline-catalyzed direct α-aminooxylation or -amination of aldehydes provides efficiently for the enantioselective synthesis of α-amino acid derivatives. The highly enantioselective method for the synthesis of γ-amino-α,β-unsaturated esters via tandem α-amination-Horner-Wadsworth-Emmons (HWE) olefination of aldehydes is described in Org. Lett., 2007, 9 (6), pp 1001-1004 by Shriram P. Kotkar et al. Further organocatalytic sequential α-aminoxylation followed by cis-Wittig olefination of aldehydes is reported by Dattatray A. Devalankar Tetrahedron: Asymmetry Volume 23 Issues 3-4, 29 Feb. 2012, Pages 240-244. The organocatalytic sequential α-amination-corey-chaykovsky reaction of aldehydes is reported by B. Senthil kumar in Org. lett., 2012, 14 (10), pp 2468-2471.

Yet, full synthetic potential of the use of α-functionalized aldehydes that are readily available in situ by existing route in excellent enantioselectivity, remains to be further explored.

In continuation of present work on the utilization and application of these enantiomerically-enriched α-functionalized aldehydes, the present inventors have succeeded to develop sequential reaction of α-aminooxylation or -amination of o-nitrohydrocinnamaldehydes followed by intramolecular catalytic hydrogenation which indeed furnish 3-hydroxy- and 3-aminated THQs in good yields with excellent enantioselectivity/optical purity.

OBJECTIVE OF THE INVENTION

The main objective of the present invention is to provide concise, environmentally benign, process for the synthesis of chiral 3-substituted tetrahydroquinoline derivatives with high yield and enantioselectivity based on proline catalyzed α-functionalization followed by reductive cyclization of substituted o-nitrohydrocinnamaldehydes.

Another objective of the present invention is to provide a process for the synthesis of (−)-sumanirole (96% ee) and 1-[(S)-3-(dimethylamino)-3,4-dihydro-6,7-dimethoxy-quinolin-1(2H)-yl]propa-none[(S)-903] (92% ee).

ABBREVIATIONS

PhNO: Nitrosobenzene

DIAD: Diisopropyl azodicarboxylate

DBAD: Di-tert-butyl azodicarboxylate (S)-903: 1-[(S)-3-(dimethylamino)-3,4-dihydro-6,7-dimethoxy quinolin-1(2H)-yl]propanone (TBDPS): tert-Butyldiphenylsilyl ether THQ: 1,2,3,4-Tetrahydroquinoline

SUMMARY OF THE INVENTION

Accordingly, the present invention provides a process for the synthesis of chiral 3-substituted tetrahydroquinoline of general formula 2 from 4,5 disubstituted o-nitrohydrocinnamaldehy of general formula 1 with high enantioselectivity (99%)

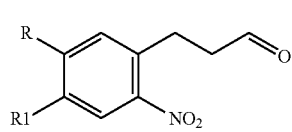

General formula 1

4,5-substituted o-nitrohydrocinnamaldehyde

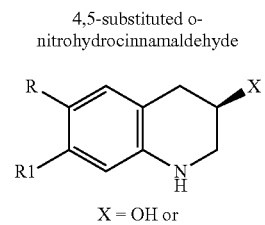

General formula 2

X = OH or
X = NCO2R2 — NHCO2R2 wherein, R and $R_1$ is independently selected from the group consisting of hydrogen, hydroxyl (C1-C6) alkyl, halogen, aryl, alkylaryl, (C1-C6) alkoxy, protecting group such as t-Butyldiphenylsilyl ether (OTBDPS), Methoxymethyl ether (O-MOM), Tosyl, Benzyl, t-Butyl carbamate (Boc) or R and R1 together form —O—CH₂—O— linkage; and 'X' is selected from —OH or disubstituted hydrazine-1,2-dicarboxylate of formula (—N—CO₂R₂—NH—CO₂R₂), wherein 'R₂' is selected from the group consisting of branched or unbranched (C1-C6) alkyl, preferably ethyl, isopropyl, t-butyl, or substituted or unsubstituted aryl preferably (4-chlorobenzyl)

wherein the said process comprising α-functionalizing of aldehyde by stirring 4,5 disubstituted o-nitrohydrocinnamaldehy, a polar aprotic organic solvent, nitrosobenzene or dialkyl azodicarboxylate in presence of D or L proline at temperature ranging between −20 to 30° C. for a period ranging between 10 min to 4 hrs followed by in situ intramolecular reductive cyclization of α-functionalized aldehyde by stirring in presence of 10% Pd/C/H₂, (1 atm) and an organic solvent at temperature ranging between 20° to 30° C. for a period ranging between 6 to 12 h to obtain chiral 3-substituted tetrahydroquinoline.

In one embodiment of the present invention the α-functionalization comprises α-aminooxylation or α-amination of 4,5 substituted o-nitrohydrocinnamaldehyde.

In another embodiment of the present invention the polar aprotic solvent is selected from the group consisting of acetonitrile (CH₃CN), methanol (MeOH), ethanol (EtOH), chloroform (CHCl₃), dichloromethane (CH₂Cl₂), tetrahydrofurane (THF), dimethylsulfoxide (DMSO) either alone or combination thereof.

In another embodiment of the present invention organic solvent used in the reductive cyclization selected from the group consisting of ethanol, methanol, propanol, isopropanol, t-butanol, pentanol, CH₃CN, THF, CH₂Cl₂ either alone or combination thereof, preferable methanol or mixture of CH₃CN/MeOH in the ratio of (1:3).

In another embodiment of the present invention the dialkylaryl azodicarboxylate is selected from the group consisting of diethyl azodicarboxylate, diisopropyl azodicarboxylate, di tert-butyl azodicarboxylate, optionally dibenzyl azodicarboxylate or di 4-chlorobenzyl azodicarboxylate.

In another embodiment of the present invention the proline is selected from D-proline or L-proline with concentration in the range of 10 to 20 mol %.

In another embodiment of the present invention yield of chiral 3-substituted tetrahydroquinoline is in the range of 70-87%.

In another embodiment of the present invention enantiomeric excess of chiral 3-substituted tetrahydroquinoline is in the range of 90-99%

In another embodiment of the present invention the chiral 3-substituted tetrahydroquinoline derivative is further converted to therapeutic agents, namely (−) sumanirole with 96% ee, and 1-[(S)-3-(dimethylamino)-3,4-dihydro-6,7-dimethoxyquinolin-1(2H)yl]propan-1-one, (S)-903 with 92% ee.

DETAIL DESCRIPTION OF THE INVENTION

The invention will now be described in detail in connection with certain preferred and optional embodiments, so that various aspects thereof may be more fully understood and appreciated. The invention relates to novel and concise process for the construction/preparation of chiral 3-substituted tetrahydroquinoline derivatives with high optical purities based on proline catalyzed asymmetric α-functionalization of aldehyde, followed by reductive cyclization under catalytic hydrogenation condition.

In the invention, the construction of chiral 3-substituted tetrahydroquinoline derivatives is provided by proline catalyzed asymmetric α-functionalization of aldehyde, wherein proline catalyst is particularly L-proline or D-proline and the substrate or starting material is easily available, non-expensive aldehyde, preferably 4,5 substituted o-nitrohydrocinnamaldehyde.

The invention particularly provides proline catalyzed asymmetric α-functionalization of 4,5 substituted o-nitrohydrocinnamaldehyde to form α-functionalized o-nitro hydrocinnamaldehyde, followed by reductive cyclization of nitro group under Pd/C catalyzed hydrogenation to incur chiral 3-substituted tetrahydroquinoline derivatives (scheme 1).

Scheme 1: Synthesis of chiral 3-substituted tetrahydoquinoline derivatives

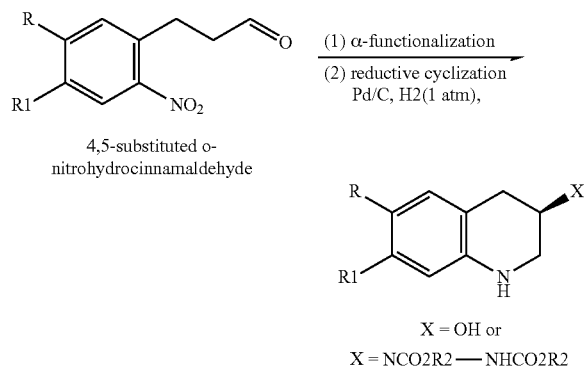

wherein, R and R1 is independently selected from the group consisting of hydrogen, hydroxyl (C1-C6) alkyl, halogen, aryl, alkylaryl, (C1-C6) alkoxy, protecting group such as t-Butyldiphenylsilyl ether (OTBDPS), Methoxymethyl ether (O-MOM), Tosyl, Benzyl, t-Butyl carbamate (Boc); or R and R1 together form —O—$CH_2$—O— linkage; and X is selected from —OH or disubstituted hydrazine-1,2-dicarboxylate i.e. (—N—$CO_2R_2$—NH—$CO_2R_2$); wherein $R_2$ is selected from the group consisting of branched or unbranached (C1-C6) alkyl, preferably isopropyl, t-butyl, ethyl, or substituted or unsubstituted aryl preferably (4-chlorobenzyl).

The α-functionalization comprises proline catalyzed α-aminooxylation or α-amination, hereinafter α-aminooxylation is referred as condition A, and α-amination is referred as condition B. Further the Condition A or α-aminooxylation comprises proline (20 mol %), nitrosobenzene in polar aprotic solvent, at 20° to 30° C.; and Condition B or α-amination comprises proline (10-20 mol %), dialkyl azodicarboxylate in polar aprotic solvent, at 0 to −20° C.

The proline catalyzed asymmetric α-functionalization of aldehyde reaction is carried out under condition A, wherein 4,5 substituted o-nitrohydrocinnamaldehyde (4) reacts with nitrosobenzene in presence of proline in suitable polar aprotic organic solvent at ambient temperature for 10 to 30 mins gives α-aminooxylated o-nitrohydrocinnamaldehyde followed by in situ intramolecular reductive cyclization in presence of 10% Pd/C/$H_2$, (1 atm) in lower alcohol at ambient temperature gives chiral 3-hydroxy THQ derivatives (5) in yield more than 70% and enantioselectivity more than 95% ee.

Scheme 2: Synthesis of chiral 3-hydroxy tetrahydroquinoline derivatives

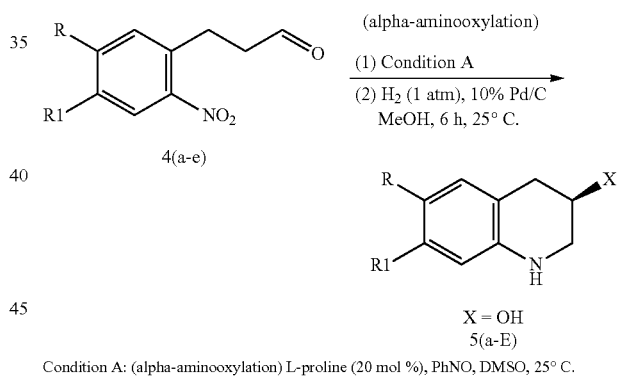

Condition A: (alpha-aminooxylation) L-proline (20 mol %), PhNO, DMSO, 25° C.

The proline is selected from either D or L-proline with molar concentration 20 mol %, whereas the ambient temperature is in the range of 20° to 30° C., preferably 25° C.

The suitable polar aprotic organic solvent employed in condition A is selected from the group consisting of acetonitrile ($CH_3CN$), methanol (MeOH), ethanol (EtOH), chloroform ($CHCl_3$), dichloromethane ($CH_2Cl_2$), tetrahydrofurane (THF), dimethylsulfoxide (DMSO) either alone or combination thereof, preferably condition A organic solvent is DMSO.

The reductive cyclization is carried out in presence of 10% Pd/C/$H_2$, (1 atm) in lower alcohol selected from ethanol, methanol, propanol, isopropanol, t-butanol, pentanol either alone or combination thereof, preferably reductive cyclization in condition A is carried out in presence of Methanol.

TABLE 1

Studies for Proline-Catalyzed α-Aminooxylation/Reductive Cyclization of o-Nitrohydrocinnamaldehyde 4a under Condition A:

Condition A[a]
S1
followed by
H₂ (1 atm),
10% Pd/C,
MeOH, 25° C.,
S2, 6 h

5a, X = OH

| entry | S1 | S2 | product (5a) yield (%)[c] | ee (%)[d] |
|---|---|---|---|---|
| 1[e] | CH₃CN | MeOH | 62 | 82 |
| 2[e] | CH₃CN | CH₃CN/MeOH | 52 | 96 |
| 3[e] | CH₂Cl₂ | CH₂Cl₂/MeOH | 35 | nd |
| 4 | CH₂Cl₂ | MeOH | 39 | nd |
| 5 | THF | MeOH | 15 | nd |
| 6 | CHCl₃ | MeOH | 30 | nd |
| 7[f] | DMSO | MeOH | 71 | 96 | wherein R1, R = H
[a]Condition A: L-proline (20 mol %), o-nitrohydrocinnamaldehyde (5 mmol), PhNO (5 mmol), 15 min.;
[c]isolated yield after column chromatography;
[d]ee determined by chiral HPLC analysis;
[e]solvent ratio (1:3);
[f]reaction was carried out at 25° C. for 10 min followed by ether extraction;
g not determined.
S1 = solvent for α-aminooxylation or -amination, S2 = solvent for reductive cyclication.

According to Table 1, the α-aminooxylation reaction of 4,5 substituted o-nitro hydrocinnamaldehyde 4a with nitrosobenzene as oxygen source was carried out in the presence of L-proline (20 mol %) in CH₃CN at −20° C. for 24 h to obtain α-aminooxylate o-nitrohydrocinnamaldehyde. Since α-aminooxy aldehydes are prone to racemization, it was immediately in situ subjected to catalytic hydrogenation [10% Pd/C, (1 atm) H₂] by distilling out CH₃CN under reduced pressure and adding MeOH into it, which gave 3-hydroxy THQ 5a in 62% yield with moderate enantioselectivity (82% ee). The low ee could possibly be due to the racemization occurring during the removal of CH₃CN at slightly elevated temperature (45° C.). To obtain high enantioselectivity, a mixed solvent system of CH₃CN/MeOH (1:3) was used, 5a was obtained in higher enantioselectivity (96% ee) with low yield (52%). In order to improve the yield of THQs, the inventors were further conducted experiments in several solvent systems (CHCl₃, CH₂Cl₂ and THF). However, there was no significant improvement in yields observed in each case. Subsequently, the best result (71% yield, 96% ee) for 5a was obtained when α-aminooxylation was carried out in DMSO and the intramolecular reductive cyclization done, in MeOH in a sequential manner at ambient temperature (entry 7; Table 1).

The L-proline catalyzed asymmetric α-functionalization of aldehyde reaction is carried out under condition B, wherein 4,5-substituted o-nitrohydrocinnamaldehyde (4) reacts with dialkyl azodicarboxylate in presence of D or L-proline (10-20 mol %) as catalyst in suitable polar aprotic organic solvent at lower temperature in the range of −20 to 0° C. for 2 to 4 hrs gives α-aminated o-nitrohydrocinnamaldehyde followed by in situ intramolecular reductive cyclization in presence of 10% Pd/C, H₂ (1 atm) in suitable organic solvent at ambient temperature gives chiral 3-aminated THQ derivatives (6) with yield more than 80% and enantioselectivity more than 90% ee.

Scheme 3: Synthesis of chiral 3-aminated tetrahydroquinoline derivatives

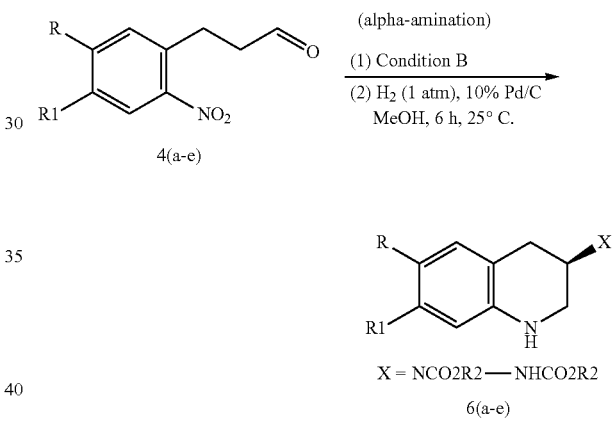

Condition B: (alpha-amination) D/L-proline (20 mol %)
R2CO2—N═N—CO2R2,
ACN, 0° C., 3 h In condition B dialkyl azodicarboxylate is used as amino source to obtain α-aminated o-nitrohydrocinnamaldehyde, wherein dialkyl azodicarboxylate is selected from the group consisting of diethyl azodicarboxylate, diisopropyl azodicarboxylate, di-tert-butyl azodicarboxylate, optionally dibenzyl azodicarboxylate or di 4-chlorobenzyl azodicarboxylate.

The suitable polar aprotic organic solvent used in condition B or amination is selected from acetonitrile (CH₃CN), methanol (MeOH), ethanol (EtOH), chloroform (CHCl₃), dichloromethane (CH₂Cl₂), tetrahydrofurane (THF), dimethylsulfoxide (DMSO) either alone or combination thereof, preferably organic solvent in condition B is CH₃CN.

Further the reductive cyclization in condition B is carried out in presence of organic solvents such as CH₃CN, Methanol, THF, CH₂Cl₂ or mixtures thereof, preferably mixture of CH₃CN/MeOH in the ratio of (1:3).

TABLE 2

Studies for Proline-Catalyzed α-Amination/Reductive Cyclization of o-Nitrohydrocinnamaldehyde 4a under Condition B:

| entry | S1 | S2 | yield (%)[c] | ee (%)[d] |
|---|---|---|---|---|
| 1[e] | CH₃CN | MeOH | 85 | 60 |
| 2[e] | CH₃CN | CH₃CN/MeOH | 82 | 90 |
| 3[e] | CH₂Cl₂ | CH₂Cl₂/MeOH | 65 | nd |
| 4 | CH₂Cl₂ | MeOH | 70 | 75 |
| 5 | THF | MeOH | 35 | nd |
| 6 | CHCl₃ | MeOH | 45 | nd |
| 7[f] | DMSO | MeOH | — | — | wherein R1, R = H
[b]Condition B: L-proline (10 mol %), o-nitrohydrocinnamaldehyde (5.5 mmol), iPrCO₂N=NCO₂iPr (5 mmol), 3 h;
[c]isolated yield after column chromatography;
[d]ee determined by chiral HPLC analysis;
[e]solvent ration (1:3);
[f]reaction was carried out at 25° C. for 10 min followed by ether extraction;
[g] not determined.
S1 = solvent for α-aminooxylation or -amination, S2 = solvent for reductive cyclization.

According to Table 2, the α-amination reaction of o-nitrohydrocinnamaldehyde nitrohydrocinnamaldehyde 4a with diisopropyl azodicarboxylate (DIAD) as amine source in presence of L-proline (10 mol %) as catalyst in CH₃CN was carried out using List's protocol that substantially gave the corresponding chiral α-aminated aldehyde in situ. The removal of CH₃CN under reduced pressure and subsequently carrying out the reductive cyclization [Pd/C, H₂ (1 atm), MeOH] afforded the desired 3-amino THQ 6a in high yield (85%) with low ee (60%). To improve the yield of 3-amino THQ the amination process, was carried out in CH₃CN and reductive cyclization in a solvent mixture of CH₃CN/MeOH (1:3), higher yield (82%) and enantioselectivity (90%) of 6a was obtained (Table 2).

Optionally other amine sources such as di-tert-butyl azodicarboxylate can be conveniently employed under the reaction condition B to afford the desired 3-aminated THQs in high yields and enantioselectivity; however, the reactions were not efficient in the case when other commercially available L-proline based catalysts were screened.

The scope of the instant reaction is established by subjecting several o-nitrohydrocinnamaldehydes 4a-e to sequential α-aminooxylation or -amination followed by reductive cyclization protocol.

TABLE 3

L-Proline-Catalyzed Sequential α-Aminooxylation or -Amination/Reductive Cyclization of o-Nitro Hydrocinnamaldehyde (4a-e)

| | | product (5a-e) | | products (6a-e) | |
|---|---|---|---|---|---|
| entry | substrates (4a-e) | yield (%)[c] | ee (%)[d] | yield (%)[c] | ee (%)[d] |
| a | R = R₁ = H | 71 | 96 | 82 | 90 |
| b | R = R₁ = OMe | 76 | 98 | 85 | 92 |
| c | R, R₁ = —O—CH₂—O— | 75 | 94 | 87 | 91 |
| d | R = O-pentyl; R₁ = OMe | 72 | 96 | 81 | 91 |
| e | R = OTBDPS; R₁ = OMe | 70 | 99 | 80 | 90 |

[a]Condition A: L-proline (20 mol %), o-nitrohydrocinnamaldehyde (5 mmol), nitroso benzene (5 mmol), DMSO (20 mL), 10 min., then ether extraction followed by H₂ (1 atm), 10% Pd/C (5 wt %), MeOH (20 mL);
[b]Condition B: L-proline (10 mol %), o-nitrohydrocinnamaldehyde (5.5 mmol), iPrCO₂N=NCO₂iPr (5 mmol), CH₃CN (10 mL), 3 h, followed by H₂ (1 atm), 10% Pd/C, MeOH (30 mL);
[c]isolated yieds of THQ-3-ol;
[d]ee determined by chiral HPLC analysis.

According to Table 3, when substrate was subjected to L-proline catalyzed α-aminooxylation or -amination with 1 equiv of PhNO or DIAD, several o-nitrohydrocinnamaldehydes 4a-e gave the corresponding (R)-3-hydroxytetrahydroquinoline 5a-e (70-76%) or (R)-3-aminotetrahydroquinoline 6a-e (80-87%) derivatives respectively with excellent enantioselectivities. For substrates with easily removable groups like TBDPS, the corresponding 3-substituted THQs were obtained in excellent enantioselectivities (entry e, Table 3).

Further, the present invention provides preparation of substrate or starting material from cinnamyl alcohol. Accordingly o-Nitrohydrocinnamaldehydes 4b-e, the starting materials, were efficiently prepared from the corresponding hydrocinnamyl alcohols 7b-e in two steps: (i) regiospecific aromatic nitration of 7b-e with conc. HNO₃ to give nitro compounds 8b-e in 80-95% yield; (ii) subsequent oxidation of nitro alcohols 4b-e with Pyridinium chlorochromate (PCC) giving in 80-85% yield (cf scheme 4).

Scheme 4: Synthesis of Substituted o-Nitrohydrocinnamaldehydes (4b-e)

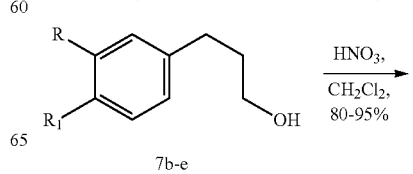

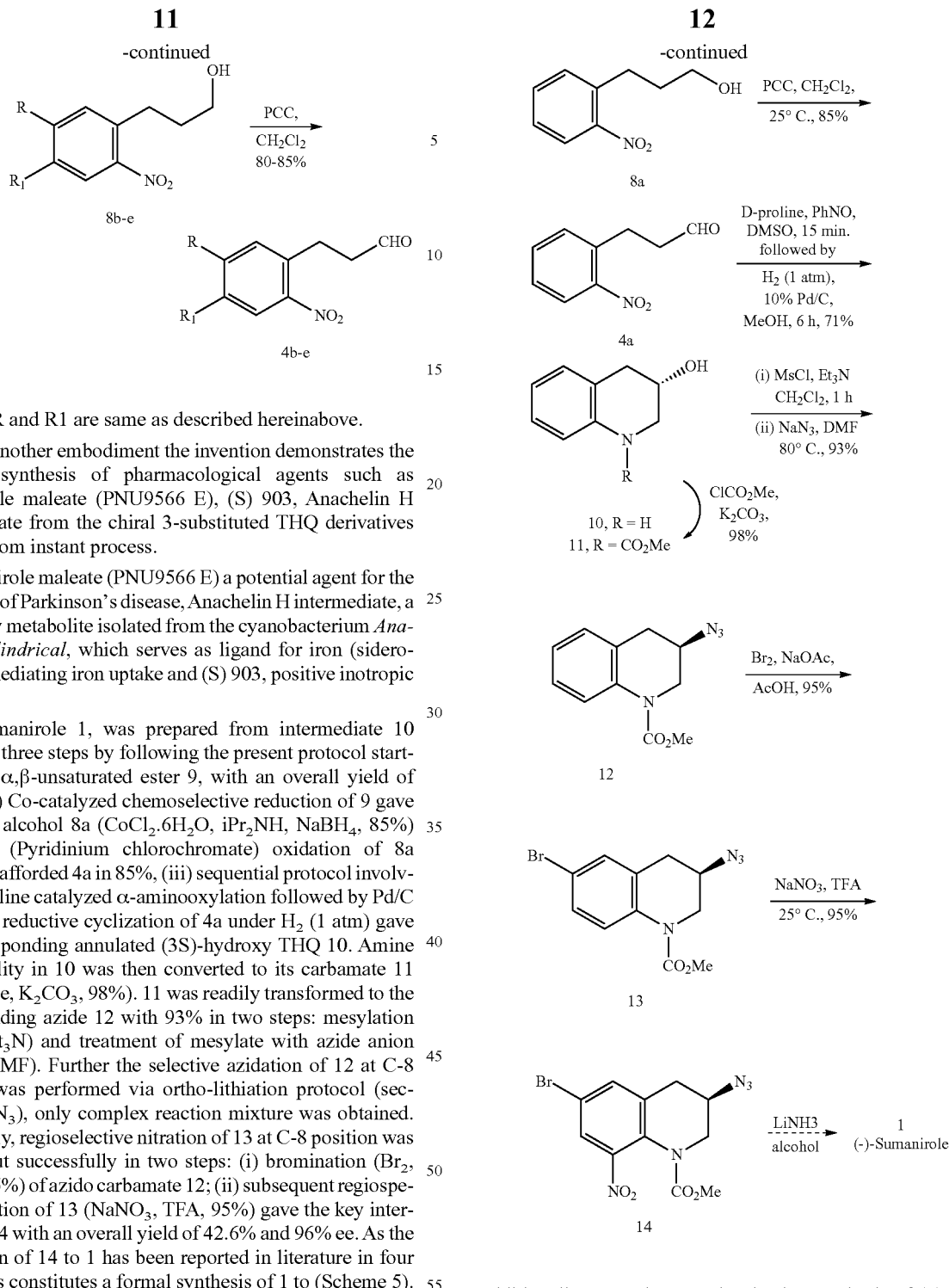

wherein R and R1 are same as described hereinabove.

In yet another embodiment the invention demonstrates the efficient synthesis of pharmacological agents such as Sumanirole maleate (PNU9566 E), (S) 903, Anachelin H intermediate from the chiral 3-substituted THQ derivatives derived from instant process.

Sumanirole maleate (PNU9566 E) a potential agent for the treatment of Parkinson's disease, Anachelin H intermediate, a secondary metabolite isolated from the cyanobacterium *Anabaena cylindrical*, which serves as ligand for iron (siderophores) mediating iron uptake and (S) 903, positive inotropic agent.

(−)-Sumanirole 1, was prepared from intermediate 10 readily in three steps by following the present protocol starting from α,β-unsaturated ester 9, with an overall yield of 52.2%: (i) Co-catalyzed chemoselective reduction of 9 gave cinnamyl alcohol 8a (CoCl$_2$.6H$_2$O, iPr$_2$NH, NaBH$_4$, 85%) (ii) PCC (Pyridinium chlorochromate) oxidation of 8a smoothly afforded 4a in 85%, (iii) sequential protocol involving D-proline catalyzed α-aminooxylation followed by Pd/C catalyzed reductive cyclization of 4a under H$_2$ (1 atm) gave the corresponding annulated (3S)-hydroxy THQ 10. Amine functionality in 10 was then converted to its carbamate 11 (ClCO$_2$Me, K$_2$CO$_3$, 98%). 11 was readily transformed to the corresponding azide 12 with 93% in two steps: mesylation (MsCl, Et$_3$N) and treatment of mesylate with azide anion (NaN$_3$, DMF). Further the selective azidation of 12 at C-8 position was performed via ortho-lithiation protocol (sec-BuLi, TsN$_3$), only complex reaction mixture was obtained. Alternately, regioselective nitration of 13 at C-8 position was carried out successfully in two steps: (i) bromination (Br$_2$, AcOH, 95%) of azido carbamate 12; (ii) subsequent regiospecific nitration of 13 (NaNO$_3$, TFA, 95%) gave the key intermediate 14 with an overall yield of 42.6% and 96% ee. As the conversion of 14 to 1 has been reported in literature in four steps, thus constitutes a formal synthesis of 1 to (Scheme 5).

Scheme 5. Formal Synthesis of (-)-Sumanirole (1)

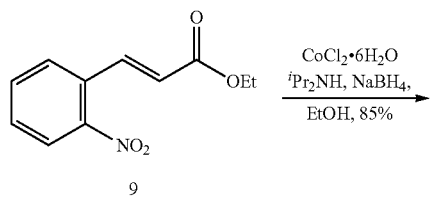

Additionally, a concise enantioselective synthesis of (S)-903 2 was undertaken to demonstrate the direct application of α-amination-reductive cyclization protocol in synthesis. Thus, 15 was prepared using D-proline as catalyst and di-tert-butyl azodicarboxylate as amine source by following the optimized condition. THQ 15 was subsequently acylated to give the corresponding amide 16 followed by Boc deprotection furnished hydrazine 17. Its hydrogenolysis under Raney Ni reduction condition and subsequent reductive methylation (HCHO, HCO$_2$H) afforded 2 in 65% yield and 92% ee (Scheme 6).

Scheme 6: Total Synthesis of [(S)-903] (2)

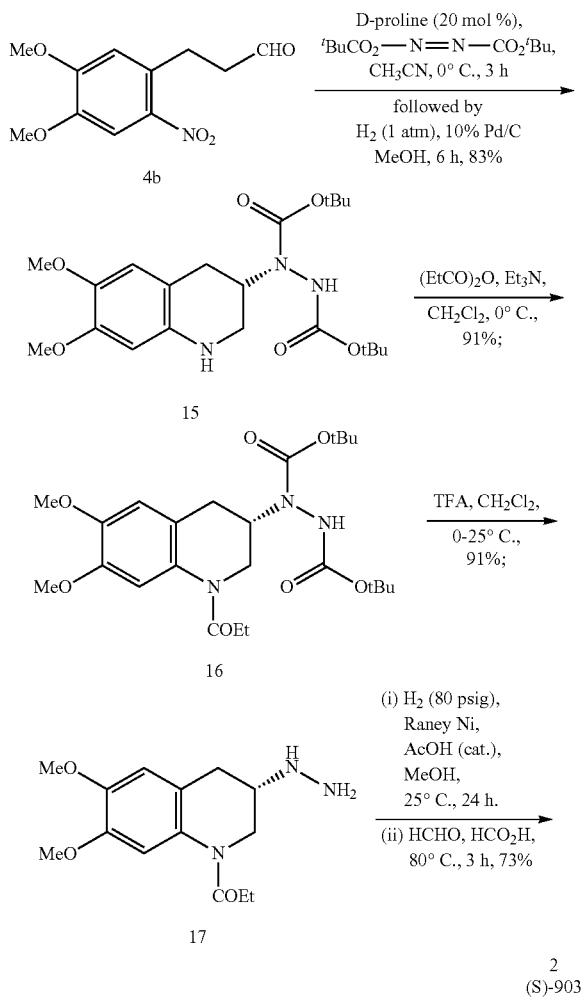

Consequently the invention provides a novel organocatalyzed sequential strategy for the construction of chiral 3-substituted THQs in high yields. Although two different catalysts organocatalyst and Pd catalyst were used for the reaction, the protocol is convenient to carry out under milder conditions with excellent enantioselectivity. Further the instant strategy has wide applications in the synthesis of optically pure 3-substituted tetrahydroquinoline derivatives 5 and 6 (X=—OH, —NH$_2$) owing to the flexible nature of synthesis of substituted o-nitrohydrocinnamaldehydes and the ready availability of both enantiomers of proline.

INDUSTRIAL ADVANTAGES

The present invention is based on non-chiral pool synthesis, where starting material is easily available, simple, non-expensive aldehyde.

Further the instant process is highly enantioselective, environmentally benign, and industrially feasible, wherein the process employs organocatalytic α-functionalization of aldehydes to generate the requisite chiral center of high optical purities in a single step.

The THQ derivatives derived from instant process are key intermediate for the synthesis of therapeutically or biologically active ingredient such as Sumanirole maleate, (S) 903, Anachelin H intermediate and like thereof.

The following examples are given by way of illustration of the working of the invention in actual practice and should not be construed to limit the scope of the to present invention in any way.

EXAMPLES

Experimental

The $^1$H NMR spectra were recorded on 200 MHz NMR spectrometer using TMS as an internal standard. The $^{13}$C NMR spectra were recorded on 200 NMR spectrometer (50 MHz). Mass spectra were taken on an MS-TOF mass spectrometer. HRMS were taken on ESI mass spectrometer. The IR spectra were recorded on an FT-IR spectrometer. Column chromatographic separations were carried out on silica gel (230-400 mesh).

Example 1

A General Experimental Procedure for the Preparation of (R)-1,2,3,4-Tetrahydro-6,7-Dialkyloxyquinolin-3-Ol (5a-e)

To a stirred solution of o-nitrohydrocinnamaldehyde 4a-e (6 mmol) and PhNO (6 mmol) in DMSO (20 mL), L-proline (20 mol %) was added at 25° C. and allowed to stir for 20 min. After completion of reaction, as indicated by the change in color from green to yellow, large excess (100 mL) of diethyl ether was poured into the reaction mixture and stirred for additional 10 min. The combined organic mixture was washed with H$_2$O (5×20 mL). The organic layer was separated and aqueous layer was extracted with diethyl ether (2×50 mL). Combined organic layers were washed with brine (5×50 mL), dried over anhydrous Na$_2$SO$_4$ and concentrated under reduced pressure to give the crude product. The crude α-aminooxylated aldehyde was dissolved in MeOH (20 mL) and to this mixture 10% Pd/C (5 wt %) was added. The reaction mixture was then stirred at 25° C. for additional 6 h. After the completion of reaction (monitored by TLC), it was filtered through celite and the solvent evaporated under reduced pressure. Chromatographic purification of the crude product [flash silica gel (230-400 mesh) and pet. ether:EtOAc:Et$_3$N (60:38:2)] gave the pure (R)-tetrahydroquinolin-3-ol derivatives 5a-e.

Example 1a (R)-1,2,3,4-Tetrahydroquinolin-3-ol (5a)

Yield: 71% (635 mg); Gum; [0]$^O_{25}$+12.3 (c 1, CHCl$_3$); 96% ee from HPLC analysis; Column: Chiracel OD-H (250× 4.6 mm), mobile phase: isopropyl alcohol/n-hexane (1090), wavelength: 254 nm, flow rate: 0.5 mL/min, conc.: 1.5 mg/mL, injection vol.: 10 μL, retention time: 30.07 min (−)-isomer, 33.89 min (+)-isomer; IR (CHCl$_3$): u$_{max}$ 753, 1312, 1500, 1604, 3370, 3413 cm$^{-1}$; $^1$H NMR (200 MHz, CDCl$_3$): δ 2.35 (br s, 1H), 2.76 (dd, J=3.7, 16.5 Hz, 1H), 3.01 (dd, J=4.3, 16.9 Hz, 1H), 3.26-3.38 (m, 2H), 4.21-4.29 (m, 1H), 6.53 (d, J=9.0 Hz, 1H), 6.65 (dt, J=1.1, 7.5 Hz, 1H), 6.97-7.05 (m, 2H); $^{13}$C NMR (50 MHz, CDCl$_3$): δ 35.3, 47.5, 63.2, 114.1, 117.9, 118.7, 126.9, 130.4, 143.5; ESIMS (m/z) 150 [M+H]$^+$; HRMS (ESI) calcd for C$_9$H$_{11}$NO [M+H]$^+$ 150.0919. found: 150.0910.

Example 2

A General Experimental Procedure for the Preparation of (R)-1,2,3,4-tetrahydro-quinolin-3-amine Derivatives (6a-e)

To a stirred solution of nitro hydrocinnamaldehyde 4a-e (5.5 mmol) and DIAD (5 mmol) in $CH_3CN$ (10 mL), L-proline (20 mol %) was added at 0° C. and allowed to stir for 3 h. After completion of reaction, as indicated by the disappearance of yellow color, was added MeOH (30 mL) and 10% Pd/C (5 wt %). The reaction mixture was then stirred at 25° C. for additional 12 h under $H_2$ atmosphere (1 atm.). After the completion of reaction (monitored by TLC), it was filtered through celite and the to solvent evaporated under reduced pressure. Chromatographic purification of the crude product over flash silica gel (230-400 mesh) and pet. ether:EtOAc gave the pure (R)-tetrahydroquinolin-3-amines 6a-e.

Example 2a (R)-Diisopropyl 1-(1,2,3,4-tetrahydroquinolin-3-yl) hydrazine-1,2-dicarboxylate (6a)

Yield: 82% (1.37 g); gum, $[\alpha]^D_{25}$ −720 (c 0.8, $CHCl_3$); 90% ee from HPLC analysis; Column: Chiracel OD-H (250× 4.6 mm), mobile phase: isopropyl alcohol/n-hexane (5:95), wavelength: 254 nm, flow rate: 0.5 mL/min, conc.: 1.5 mg/mL, injection vol.: 10 μL, retention time: 31.73 min (−)-isomer, 34.6 min (+)-isomer; IR ($CHCl_3$): 1107, 1180, 1230, 1246, 1306, 1375, 1408, 1511, 1711, 1721, 2932, 2981, 3298 $cm^{-1}$; $^1H$ NMR (200 MHz, $CDCl_3$): δ 1.23-1.28 (m, 12H), 2.97-3.47 (m, 4H), 4.62 (brs, 1H), 4.94-5.00 (m, 2H), 6.37 (brs, 1H), 6.48 (d, J=7.4 Hz, 1H), 6.61 (t, J=7.2 Hz, 1H), 6.96 (m, 2H) $^{13}C$ NMR (50 MHz, $CDCl_3$): δ 21.8, 21.9, 30.0, 44.5, 51.0, 69.7, 70.1, 96.0, 113.9, 117.4, 119.5, 126.8, 129.5, 143.5, 155.2, 156.6; HRMS (ESI, mz): Calculated for $C_{17}H_{25}N_3O_4$ (M+H)+ 336.1923. found: 336.1923; Analysis: $C_{17}H_{25}N_3O_4$ requires: C, 60.88; H, 7.51; N, 12.53. found: C, 60.88; H, 7.51; N, 12.53%.

Example 3

A General Experimental Procedure for the Preparation of o-nitrohydrocinnamyl Alcohol (8b-e)

To a stirred solution of alcohol 7b-e (10 mmol) in $CH_2Cl_2$ (40 mL), conc. $HNO_3$ (2 mL, d=1.4) was added dropwise at 0° C. Reaction mixture was stirred for 30 min and the progress of reaction was monitored by TLC. After completion of reaction, 50 mL of water was added. Organic layer was separated and aqueous layer was extracted with $CH_2Cl_2$ (2×50 mL). Combined organic layers were washed with brine (50 mL), dried over anhydrous $Na_2SO_4$ and then passed through a thick pad of silica gel (230-400 mesh) with $CH_2Cl_2$ as eluent. The organic layer was concentrated under reduced pressure to give 8b-e in pure form.

Example 4

3-(4,5-Dimethoxy-2-nitrophenyl)propan-1-ol (8b)

Yield: 95% (2.3 g); gum, IR ($CHCl_3$): $u_{max}$ 745, 945, 1120, 1378, 3412 $cm^{-1}$; $^1H$ NMR (200 MHz, $CDCl_3$): 1.87-1.95 (m, 2H), 2.97-3.05 (m, 2H), 3.71 (t, J=6.2 Hz, 2H), 3.92 (s, 3H), 3.94 (s, 3H), 6.74 (s, 1H), 7.57 (s, 1H); $^{13}C$ NMR (50 MHz, $CDCl_3$): δ 30.1, 33.5, 56.2, 61.9, 108.2, 113.4, 132.4, 141.2, 147.2, 153.0; Anal. Calcd for $C_{11}H_{15}NO_5$ requires C, 54.77; H, 6.27; N, 5.81. found C, 54.86; H, 6.33; N, 5.87%.

Example 5

3-(6-Nitrobenzo[1,3]dioxol-5-yl)propan-1-01 (8c)

Yield: 93% (2.1 g); gum, IR ($CHCl_3$): $u_{max}$ 857, 968, 1060, 1460, 3498 $cm^{-1}$; $^1H$ NMR (200 MHz, $CDCl_3$): δ 1.82-1.96 (m, 3H), 2.91-2.99 (m, 2H), 3.73 (t, J=6.2 Hz, 2H), 6.08 (s, 2H), 6.76 (s, 1H), 7.46 (s, 1H); $^{13}C$ NMR (50 MHz, $CDCl_3$): δ 30.1, 33.4, 61.8, 102.7, 105.7, 110.6, 134.4, 142.8, 146.3, 151.6; Anal. Calcd for $C_{10}H_{11}NO_5$ requires C, 53.33; H, 4.92; N, 6.22. found C, 53.43; H, 4.98; N, 6.27%.

Example 6

3-(4-(Cyclopentyloxy)-5-methoxy-2-nitrophenyl) propan-1-ol (8d)

Yield: 87% (2.6 g); gum, IR ($CHCl_3$): $u_{max}$ 754, 1129, 1324, 1460, 3467 $cm^{-1}$; $^1H$ NMR (200 MHz, $CDCl_3$): δ 1.58 (br s, 1H), 1.82-2.03 (m, 10H), 3.01 (t, J=7.5 Hz, 2H), 3.72 (t, J=6.0 Hz, 2H), 3.92 (s, 3H), 4.78-4.82 (m, 1H), 6.71 (s, 1H), 7.56 (s, 1H); $^{13}C$ NMR (50 MHz $CDCl_3$): 23.9, 30.0, 32.5, 33.3, 56.0, 61.7, 80.6, 110.7, 113.5, 131.9, 140.8, 145.6, 153.8; Anal. Calcd for $C_{15}H_{21}NO_5$ requires C, 61.00; H, 7.17; N, to 4.74. found C, 61.08; H, 7.23; N, 4.75%.

Example 7

3-(4-(tert-Butyldiphenylsilyloxy)-5-methoxy-2-nitrophenyl)propan-1-ol (8e)

Yield: 80% (3.7 g); gum, IR ($CHCl_3$): $u_{max}$ 907, 1172, 1068, 1531, 3367 $cm^{-1}$, $^1H$ NMR (200 MHz, $CDCl_3$): δ 1.13 (s, 9H), 1.31 (br s, 1H), 1.61-1.71 (m, 2H), 2.93 (t, J=7.4 Hz, 2H), 3.54 (s, 3H), 3.65 (t, J=6.1 Hz, 2H), 6.55 (s, 1H), 7.34-7.44 (m, 8H), 7.64-7.69 (m, 4H); $^{13}C$ NMR (50 MHz $CDCl_3$): δ 19.9, 26.7, 30.1, 33.5, 55.3, 62.0, 113.7, 117.2, 127.7, 130.0, 132.5, 132.8, 135.3, 141.1, 143.2, 154.6; Anal. Calcd for $C_{26}H_{31}NO_5Si$ requires C, 67.07; H, 6.71; N, 3.01. found C, 67.12; H, 6.73; N, 3.09%.

Example 8

A General Experimental Procedure for the Oxidation of Alcohols (4a-e)

To a stirred solution of alcohol 8a-e (5 mmol) in dry $CH_2Cl_2$ (10 mL), Pyridinium chlorochromate (PCC) (10 mmol) was added slowly at 25° C. It was then stirred for further 6 h. After completion of the reaction (monitored by TLC), it was passed through a short pad of silica gel (230-400 mesh) using $CH_2Cl_2$ as eluent. The combined organic layers were concentrated under reduced pressure to give the aldehyde 4a-e which was pure enough to be used in the next step.

Example 9

3-(2-Nitrophenyl)propanal (4a)

Yield: 85% (761 mg); gum; IR ($CHCl_3$): $u_{max}$ 765, 1166, 1225, 1235, 1454, 1712, 2989, 3123; NMR (200 MHz, $CDCl_3$): δ 2.89 (t, J=7.3 Hz, 2H), 3.20 (t, J=7.3 Hz, 2H), 7.28-7.59 (m, 3H), 7.92 (d, J=7.9 Hz, 1H), 9.82 (s, 1H); $^{13}C$ NMR (50 MHz, CDCl$_3$): 25.6, 44.4, 124.9, 127.5, 132.3, 133.1, 135.7, 199.9; Anal. Calcd for C$_9$H$_9$NO$_3$ requires: C, 60.33; H, 5.06; N, 7.82. found: C, 60.45; H, 5.13; N, 7.91%.

Example 10

3-(4,5-Dimethoxy-2-nitrophenyl)propanal (4b)

Yield: 85% (1.07 g); gum; IR (CHCl$_3$): u$_{max}$ 1155, 1215, 1278, 1371, 1720, 2935, 2983 cm$^{-1}$; $^1$H NMR (200 MHz, CDCl$_3$): δ 2.91 (t, J=7.1 Hz, 2H), 3.23 (t, J=7.3 Hz, 2H), 3.94 (s, 3H), 3.97 (s, 3H), 6.82 (s, 2H), 7.61 (s, 1H), 9.83 (s, 1H); $^{13}$C NMR (50 MHz, CDCl$_3$): δ 26.4, 44.4, 56.2, 108.1, 113.8, 131.0, 140.8, 147.4, 153.1, 200.4; Anal. Calcd for C$_{11}$H$_{13}$NO$_5$ requires: C, 55.23; H, 5.48; N, 5.86. found: C, 55.29; H, 5.57; N, 5.90%.

Example 11

3-(6-Nitrobenzo[d][1,3]dioxol-5-yl)propanal (4c)

Yield: 85% (948 mg); gum; IR (CHCl$_3$): u$_{max}$ 1253, 1348, 1496, 1608, 1718, 2987 cm$^{-1}$; $^1$H NMR (200 MHz, CDCl$_3$): δ 2.84 (t, J=7.2 Hz, 1H), 3.17 (t, J=7.0 Hz, 1H), 6.10 (s, 2H), 6.80 (s, 1H), 7.51 (s, 1H), 9.82 (s, 1H); $^{13}$C NMR (50 MHz, CDCl$_3$): δ 26.4, 44.4, 102.8, 105.7, 110.7, 133.0, 146.6, 151.7, 200.1; Anal. Calcd for C$_{10}$H$_9$NO$_5$ requires: C, 53.82; H, 4.06; N, 6.28. found: C, 53.72; H, 3.93; N, 6.21%.

Example 12

3-(4-(Cyclopentyloxy)-5-methoxy-2-nitrophenyl) propanal (4d)

Yield: 82% (1.20 g); gum; IR (CHCl$_3$): u$_{max}$ 1233, 1312, 1608, 1718, 2913, 3018 cm$^{-1}$; $^1$H NMR (200 MHz, CDCl3): 1.64-2.02 (m, 8H), 2.90 (t, J=6.9 Hz, 2H), 3.21 (t, J=7.2 Hz, 2H), 3.92 (s, 3H), 4.76-4.84 (m, 1H), 6.78 (s, 1H), 7.59 (s, 1H), 9.83 (s, 1H); $^{13}$C NMR (50 MHz, CDCl$_3$): δ 23.9, 26.3, 32.5, 44.4, 56.0, 80.6, 110.6, 113.9, 127.2, 130.0, 130.4, 137.2, 140.6, 145.9, 153.9, 200.2; Anal. Calcd for C$_{15}$H$_{19}$NO$_5$ requires: C, 61.42; H, 6.53; N, 4.78. found: C, 61.46; H, 6.48; N, 4.87%.

Example 13

3-(4-(tert-Butyl diphenyl silyloxy)-5-methoxy-2-nitrophenyl)propanal (4e)

Yield: 80% (1.85 g); gum; IR (CHCl$_3$): IR(CHCl$_3$): u$_{max}$ 1155, 1215, 1357, 1718, 2984 cm$^{-1}$; $^1$H NMR (200 MHz, CDCl$_3$): δ 1.12 (s, 9H), 2.82 (t, J=7.1 Hz, 2H), 3.13 (t, J=7.2 Hz, 2H), 3.56 (s, 3H), 6.61 (s, 1H), 7.34-7.39 (m, 8H), 7.64-7.68 (m, 4H), 9.78 (s, 1H); $^{13}$C NMR (50 MHz, CDCl$_3$): δ 19.8, 26.5, 26.7, 44.6, 55.4, 114.2, 117.2, 127.7, 130.0, 131.4, 132.6, 135.3, 143.5, 154.8, 200.6; Anal. Calcd for C$_{26}$H$_{29}$NO$_5$Si requires: C, 67.36; H, 6.31; N, 3.02. found: C, 67.43; H, 6.41; N, 3.09%.

Example 14

A General Experimental Procedure for the Preparation of (R)-1,2,3,4-tetrahydroquinolin-3-ol Derivatives (5a-e)

To the stirred solution of o-nitrohydrocinnamaldehyde 4a-e (6 mmol) and PhNO (6 mmol) in DMSO (20 mL), L-proline (20 mol %) was added at 25° C. and allowed to stir for 20 min. After completion of reaction, as indicated by the change in color from green to yellow, large excess (200 mL) of diethyl ether was poured into the reaction mixture and stirred for additional 10 min. The combined organic mixture was washed with H$_2$O (5×20 mL). The organic layer was separated and aqueous layer was extracted with diethyl ether (2×50 mL). Combined organic layers were washed with brine (5×50 mL), dried over anhydrous Na$_2$SO$_4$ and concentrated under reduced pressure to give the crude product. The crude α-aminooxylated aldehyde was dissolved in MeOH (20 mL) and to this mixture 10% Pd/C (5 wt %) was added. The reaction mixture was then stirred at 25° C. for additional 6 h. After the completion of reaction (monitored by TLC), it was filtered through celite (MeOH eluent) and the solvent evaporated under reduced pressure. Chromatographic purification of the crude product [flash silica gel (230-400 mesh) and petroleum ether:EtOAc:Et$_3$N (60:38:2)] gave the pure (R)-tetrahydroquinolin-3-ol derivatives to 5a-e.

Example 15

(R)-1,2,3,4-Tetrahydroquinolin-3-ol (5a)

Yield: 71% (635 mg); Gum; [α]$^D_{25}$ +12.3 (c 1, CHCl$_3$); Optical purity 96% ee from HPLC analysis; Column: Chiracel OD-H (250×4.6 mm), mobile phase: isopropylalcohol/n-hexane (1090), wavelength: 254 nm, flow rate: 0.5 mL/min, conc.: 1.5 mg/mL, injection vol.: 10 uL, retention time: 30.073 min (−)-isomer, 33.890 min (+)-isomer; IR (CHCl$_3$): u$_{max}$ 753, 1312, 1500, 1604, 3370, 3413 cm$^{-1}$, $^1$H NMR (200 MHz, CDCl$_3$): δ 2.35 (br s, 1H), 2.76 (dd, J=3.7, 16.5 Hz, 1H), 3.01 (dd, J=4.3, 16.9 Hz, 1H), 3.26-3.38 (m, 2H), 4.21-4.29 (m, 1H), 6.53 (d, J=9.0 Hz, 1H), 6.65 (dt, J=1.1, 7.5 Hz, 1H), 6.97-7.05 (m, 2H); $^{13}$C NMR (50 MHz, CDCl$_3$): δ 35.3, 47.5, 63.2, 114.1, 117.9, 118.7, 126.9, 130.4, 143.5; ESIMS (m/z) 150 [M+H]$^+$; HRMS (ESI) calcd for C$_9$H$_{11}$NO [M+H]$^+$ 150.0919. found 150.0910.

Example 16

(R)-1,2,3,4-Tetrahydro-6,7-dimethoxyquinolin-3-ol (5b)

Yield: 76% (954 mg); Gum; [α]$^D_{25}$ +27.1 (c 1.26, CHCl$_3$); Optical purity 98% ee from HPLC analysis; Column: Chiracel OD-H (250×4.6 mm), mobile phase: isopropylalcohol/n-hexane (2080), wavelength: 254 nm, flow rate: 0.5 mL/min, conc.: 1.5 mg/mL, injection vol.: 10 uL, retention time: 34.543 min (−)-isomer, 40.990 min (+)-isomer; IR (CHCl$_3$): u$_{max}$ 756, 1217, 1464, 1519, 3456 cm$^{-1}$; $^1$H NMR (200 MHz, CDCl$_3$): δ 2.71 (dd, J=3.9, 16.5 Hz, 1H), 2.85-3.00 (m, 1H), 3.19-3.22 (m, 2H), 3.78 (s, 3H), 3.79 (s, 3H), 4.15-4.23 (m, 1H), 6.12 (s, 1H), 6.50 (s, 1H); $^{13}$C NMR (50 MHz, CDCl$_3$): δ 34.7, 47.6, 55.6, 56.4, 63.3, 99.8, 110.5, 114.2, 136.7, 142.2, 148.0; ESIMS (m/z) 210 [M+H]$^+$; HRMS (ESI) calcd for C$_{11}$H$_{15}$NO$_3$ [M+H]$^+$ 210.1130. found 210.1108.

Example 17

(R)-5,6,7,8-Tetrahydro-[1,3]dioxolo[4,5-g]quinolin-7-ol (5c)

Yield: 75% (869 mg); Gum; [α]$^D_{25}$ +28.2 (c 1, CHCl$_3$); Optical purity 94% ee from HPLC analysis; Column: Chiracel OD-H (250×4.6 mm), mobile phase: isopropylalcohol/n-hexane (2080), wavelength: 254 nm, flow rate: 0.5 mL/min, conc.: 1.5 mg/mL, injection vol.: 10 uL, retention time: 27.200 min (−)-isomer, 30.607 min (+)-isomer; IR (CHCl$_3$): u$_{max}$ 1037, 1215, 1484, 2853, 2924, 3355 cm$^{-1}$; $^1$H NMR (200 MHz, CDCl$_3$): δ 2.16 (br s, 2H), 2.65 (dd, J=3.5, 16.7 Hz, 1H), 2.92 (dd, J=4.2, 16.7 Hz, 1H), 3.21-3.23 (m, 2H), 4.17-4.25 (m, 1H), 5.82 (s, 2H), 6.15 (s, 1H), 6.48 (s, 1H); $^{13}$C NMR (50 MHz, CDCl$_3$): δ 35.1, 47.5, 63.1, 96.4, 100.1, 109.5, 110.6, 137.9, 139.9, 146.1; ESIMS (m/z) 194 [M+H]$^+$; Anal. Calcd for C$_{10}$H$_{11}$NO$_3$ requires C, 62.17; H, 5.74; N, 7.25. found C, 62.11; H, 5.81; N, 7.30%.

Example 18

(R)-7-(Cyclopentyloxy)-6-methoxy-1,2,3,4-tetrahydroquinolin-3-ol (5d)

Yield: 72% (1.14 g); Gum; [α]$^D_{25}$ +25.7 (c 1, CHCl$_3$); Optical purity 96% ee from HPLC analysis; Column: Chiracel OD-H (250×4.6 mm), mobile phase: isopropylalcohol/n-hexane (5050), wavelength: 254 nm, flow rate: 0.5 mL/min, conc.: 1.5 mg/mL, injection vol.: 10 uL, retention time: 10.233 min (−)-isomer, 11.197 min (+)-isomer; IR (CHCl$_3$): u$_{max}$ 769, 1217, 1456, 1504, 2927, 3402 cm$^{-1}$; $^1$H NMR (200 MHz, CDCl$_3$): δ 1.55-1.83 (m, 8H), 2.72 (dd, J=3.5, 16.5 Hz, 1H), 2.91-2.99 (m, 3H), 3.21-3.23 (m, 2H), 3.76 (s, 3H), 4.16-4.23 (m, 1H), 4.59-4.65 (m, 1H), 6.11 (s, 1H), 6.52 (s, to 1H); $^{13}$C NMR (50 MHz, CDCl$_3$): δ 23.5, 32.4, 34.7, 47.6, 55.5, 63.3, 81.4, 99.7, 110.4, 119.1, 137.7, 139.7, 149.5; ESIMS (m/z) 264 [M+H]$^+$; Anal. Calcd for C$_{15}$H$_{21}$NO$_3$ requires: C, 68.42; H, 8.04; N, 5.32. found: C, 68.38; H, 8.10; N, 5.39%.

Example 19

(R)-7-(tert-Butyldiphenylsilyloxy)-6-methoxy-1,2,3,4-tetrahydroquinolin-3-ol (5e)

Yield: 70% (1.82 g); Gum; [α]$^D_{25}$+21.3 (c 1, CHCl$_3$); Optical purity 99% ee from HPLC analysis; Column: Chiracel OD-H (250×4.6 mm), mobile phase: isopropylalcohol/n-hexane (2.597.5), wavelength: 254 nm, flow rate: 0.5 mL/min, conc.: 1.5 mg/mL, injection vol.: 10 uL, retention time: 17.103 min (−)-isomer, 19.443 min (+)-isomer; IR (CHCl$_3$): u$_{max}$ 758, 1226, 1517, 2856, 2929, 3392 cm$^{-1}$; $^1$H NMR (200 MHz, CDCl$_3$): δ 1.10 (s, 9H), 2.59 (dd, J=3.9, 14.5 Hz, 1H), 2.86 (dd, J=3.7, 14.3 Hz, 1H), 3.03-3.51 (m, 2H), 3.5.1 (s, 3H), 4.08-4.16 (m, 1H), 5.90 (s, 1H), 6.42 (s, 1H), 7.31-7.39 (m, 6H), 7.69-7.73 (m, 4H); $^{13}$C NMR (50 MHz, CDCl$_3$): δ 19.8, 26.7, 29.7, 35.1, 47.6, 56.7, 63.5, 107.0, 116.0, 127.5, 129.6, 133.7, 135.4, 1370.3, 143.7, 144.5; ESIMS (m/z) 434 [M+H]$^+$; Anal. Calcd for C$_{26}$H$_{31}$NO$_3$Si requires C, 72.02; H, 7.21; N, 3.23. found C, 72.09; H, 7.18; N, 3.27%.

Example 20

A General Experimental Procedure for the Preparation of (R)-1,2,3,4-tetrahydroquinolin-3-amine Derivatives (6a-e)

To the stirred solution of nitro hydrocinnamaldehyde 4a-e (5.5 mmol) and DIAD (5 mmol) in CH$_3$CN (10 mL), L-Proline (20 mol %) was added at 0° C. and allowed to stir for 3 h. After completion of reaction, as indicated by the disappearance of yellow color, was added MeOH (30 mL) and 10% Pd/C (5 wt %). The reaction mixture was then stirred at 25° C. for additional 12 h under H$_2$ atmosphere (balloon pressure). After the completion of reaction (monitored by TLC), it was filtered through celite (MeOH eluent) and the solvent evaporated under reduced pressure. Chromatographic purification of the crude product [flash silica gel (230-400 mesh) and petroleum ether:EtOAc gave the pure (R)-tetrahydroquinolin-3-amines 6a-e.

Example 21

(R)-Diisopropyl 1-(1,2,3,4-tetrahydroquinolin-3-yl)hydrazine-1,2-dicarboxylate (6a)

Yield: 82%; gum, [α]$^D_{25}$ −720.0 (c 0.8, CHCl$_3$); HPLC analysis; Column: Chiracel OD-H (250×4.6 mm), mobile phase: isopropylalcohol/n-hexane (595), wavelength: 254 nm, flow rate: 0.5 mL/min, conc.: 1.5 mg/mL, injection vol.: 10 uL, retention time: 37.73 min (−)-isomer, 44.6 min (+)-isomer; IR (CHCl$_3$): 1107, 1180, 1230, 1246, 1306, 1375, 1408, 1511, 1711, 1721, 2932, 2981, 3298 cm$^{-1}$; $^1$H NMR (200 MHz, CDCl$_3$): δ 1.23-1.28 (m, 12H), 2.97-3.47 (m, 4H), 4.62 (brs, 1H), 4.94-5.00 (m, 2H), 6.37 (brs, 1H), 6.48 (d, J=7.43, 1H), 6.61 (t, J=7.19, 15.11, 1H), 6.96 (m, 2H) $^{13}$C NMR (50 MHz, CDCl$_3$): δ 21.86, 21.98, 30.0, 44.5, 51.0, 69.7, 70.1, 96.0, 113.9, 117.4, 119.5, 126.8, 129.5, 143.5, 155.2, 156.6; HRMS (ESI, mz): Calculated for C$_{17}$H$_{25}$N$_3$O$_4$Na (M+Na)+ 336.1923. found 336.1923; Analysis: C$_{17}$H$_{25}$N$_3$O$_4$ requires: C, 60.88; H, 7.51; N, 12.53. found: C, 60.88; H, 7.51; N, 12.53%.

Example 22

(R)-diisopropyl 1-(6,7-dimethoxy-1,2,3,4-tetrahydroquinolin-3-yl) hydrazine-1,2-di-carboxylate (6b)

Yield: 85%; gum, [c]$^D_{25}$ −1379.0 (c 1.2, CHCl$_3$); HPLC analysis; Column: Chiracel OD-H (250×4.6 mm), mobile phase: isopropylalcohol/n-hexane (595), to wavelength: 254 nm, flow rate: 0.5 mL/min, conc.: 1.5 mg/mL, injection vol.: 10 uL, retention time: 19.3 min (−)-isomer, 22.3 min (+)-isomer; IR (CHCl$_3$): 1036, 1108, 1133, 1179, 1385, 1398, 1519, 1707, 2999, 3313, 3378 cm$^{-1}$; $^1$H NMR (200 MHz, CDCl$_3$): δ 1.22-128 (m, 12H), 2.81-2.93 (m, 2H), 3.20-3.41 (m, 2H), 3.77 (s, 3H), 3.79 (s, 3H), 4.54-4.58 (m, 1H), 4.94-4.97 (m, 2H), 6.11 (s, 1H), 6.32 (br. s, 1H), 6.50 (s, 1H); $^{13}$C NMR (50 MHz, CDCl$_3$): δ 22.0, 29.6, 44.9, 51.6, 56.5, 69.2, 70.0, 96.1, 99.6, 111.2, 113.7, 137.5, 141.7, 148.3, 155.3, 156.7; HRMS (ESI, mz): Calculated for C$_{19}$H$_{29}$N$_3$O$_6$Na (M+Na)+ 396.2135. found 396.2131; Analysis: C$_{19}$H$_{29}$N$_3$O$_6$ requires: C, 57.71; H, 7.39; N, 10.63. found: C, 57.72; H, 7.33; N, 10.67%.

Example 23

(R)-diisopropyl 1-(5,6,7,8-tetrahydro-[1,3]dioxolo[4,5-g]quinolin-7-yl)hydrazine-1,2-dicarboxylate (6c Yield: 87%; gum, [α]$^D_{25}$ −1694.1 (c 0.7, CHCl$_3$); HPLC analysis; Column: Chiracel OD-H (250×4.6 mm), mobile phase: isopropylalcohol/n-hexane (595), wavelength: 254 nm, flow rate: 0.5 mL/min, conc.: 1.5 mg/mL, injection vol.: 10 uL, retention time: 20.3 min (−)-isomer, 27.9 min (+)-isomer; IR (CHCl$_3$): 1038, 1106, 1161, 1182, 1216, 1235, 1299, 1374, 1386, 1468, 1503, 1707, 2916, 2980, 3304 cm$^{-1}$; $^1$H NMR (200 MHz, CDCl$_3$): δ 1.23-1.28 (m, 12H), 2.82-2.98 (m, 2H), 3.13-3.42 (m, 2H), 4.51 (m, 1H), 4.94-4.97 (m, 2H), 5.30 (s, 1H), 5.80 (s, 2H), 6.09 (s, 1H), 6.28 (br. s, 1H), 6.44 (s, 1H); $^{13}$C NMR (50 MHz, CDCl$_3$): δ 21.9, 29.8, 44.7, 51.3, 69.4, 70.0, 96.6, 108.9, 111.6, 137.5, 139.9, 146.3, 155.0, 156.6; Analysis: C$_{18}$H$_{25}$N$_3$O$_6$ requires: C, 56.98; H, 6.64; N, 11.08. found: C, 56.98; H, 6.64; N, 11.08%.

Example 24

(R)-diisopropyl-1-(7-(cyclopentyloxy)-6-methoxy-1,2,3,4-tetrahydroquinolin-3-yl)hydrazine-1,2-dicarboxylate (6d)

Yield: 81%; gum, $[\alpha]^D25$-327.6 (c 3.4, CHCl$_3$); HPLC analysis; Column: Chiracel OD-H (250×4.6 mm), mobile phase: isopropylalcohol/n-hexane (595), wavelength: 254 nm, flow rate: 0.5 mL/min, conc.: 1.5 mg/mL, injection vol.: 10 uL, retention time: 29.9 min (−)-isomer, 37.6 min (+)-isomer; IR (CHCl$_3$): 1035, 1108, 1135, 1198, 1227, 1253, 1299, 1340, 1374, 1385, 1397, 1515, 1712, 2978, 3296 cm$^{-1}$; $^1$H NMR (200 MHz, CDCl$_3$): δ 1.23-128 (m, 1H), 1.56-1.82 (m, 1H), 2.75-3.37 (m, 4H), 3.75 (s, 3H), 4.59 (m, 2H), 4.94-5.00 (m, 2H), 6.01 (s, 1H), 6.28 (br. s, 1H), 6.51 (s, 1H); $^{13}$C NMR (50 MHz, CDCl$_3$): δ 21.8, 22.0, 24.9, 29.6, 44.8, 51.2, 56.8, 69.4, 69.8, 80.1, 103.1, 111.1, 114.9, 137.4, 142.8, 146.8, 155.0, 156.5; Analysis: C$_{23}$H$_{35}$N$_3$O$_6$ requires: C, 61.45; H, 7.85; N, 9.35. found: C, 61.45; H, 7.85; N, 9.35%.

Example 25

(R)-1,2,3,4-Tetrahydro-6,7-dimethoxyquinolin-3-amine (6e)

Yield: 80%; gum, $[\alpha]^D_{25}$ −434.5 (c 3.2, CHCl$_3$); HPLC analysis; Column: Chiracel OD-H (250×4.6 mm), mobile phase: isopropylalcohol/n-hexane (595), wavelength: 254 nm, flow rate: 0.5 mL/min, conc.: 1.5 mg/mL, injection vol.: 10 uL, retention time: 35.5 min (−)-isomer, 41.990 min (+)-isomer; IR (CHCl$_3$): 702, 1109, 1143, 1228, 1255, 1298, 1385, 1518, 1710, 2856, 2931, 2979, 3283 cm$^{-1}$; $^1$H NMR (200 MHz, CDCl$_3$): δ 1.25 (t, J=4.5, 12.8 Hz, 1H), 2.93 (m, 1H), 3.20-3.40 (m, 2H), 3.77 (s, 3H), 3.79 (s, 3H), 4.55 (m, 1H), 4.94 (m, 2H), 6.11 (s, 1H), 6.32 (brs, 1H), 6.50 (s, 1H); $^{13}$C NMR (50 MHz, CDCl$_3$): 619.73, 21.93, 26.63, 29.59, 51.20, 56.54, 69.45, 69.70, 107.10, 115.11, 127.44, 129.47, 133.65, 135.25, 137.25, 143.20, 144.29; Analysis: C$_{34}$H$_{45}$N$_3$O$_6$Si requires: C, 65.88; H, 7.32; N, 6.78. found: C, 65.88; H, 7.32; N, 6.78%.

Example 26

2-(2-Nitrophenyl)ethanol (8a)

To a stirred solution of ester 9 ((E)-ethyl 3-(2-nitrophenyl) acrylate) (7.0 g, 31.7 mmol), CoCl$_2$.6H$_2$O (377 mg, 5 mol %) and diisopropyl amine (320 mg, 10 mol %) in 95% ethanol (100 mL) was added NaBH$_4$ (4.8 g, 126.8 mmol) slowly at 25° C. It was then stirred for 24 h at 50° C. After completion of the reaction (monitored by TLC), it was quenched with addition of water (20 mL) and ethyl acetate (100 mL). The organic layer was separated and the aqueous layer extracted with ethyl acetate (2×50 mL). The combined organic layers were washed with brine (2×20 mL), dried over anhydrous Na$_2$SO$_4$ and concentrated under reduced pressure to give the crude product. Chromatographic purification of crude product with petroleum etherethyl acetate (7:3 v/v) afforded alcohol 8a (5.74 g) as gum.

Yield: 85%; IR (CHCl$_3$): u$_{max}$ 857, 968, 1029, 1060, 1245, 1440, 1507, 3430 cm$^{-1}$; $^1$H NMR (200 MHz, CDCl$_3$): δ 1.85-1.99 (m, 2H), 2.14 (br s, 1H), 2.98 (t, J=7.6 Hz, 2H), 3.70 (t, J=6.2 Hz, 2H), 7.31-7.55 (m, 3H), 7.86 (d, J=7.7 Hz, 1H); $^{13}$C NMR (50 MHz, CDCl$_3$): δ 29.1, 33.2, 61.6, 124.4, 126.8, 131.8, 132.8, 136.7, 149.1. Anal. Calcd for C$_9$H$_{11}$NO$_3$ requires C, 59.66; H, 6.12; N, 7.73. found C, 59.71; H, 6.15; N, 7.79%.

Example 27

3-(2-Nitrophenyl)propanal (4a)

To a stirred solution of alcohol 8a (5 g, 27.60 mmol) in dry CH$_2$Cl$_2$ (100 mL), PCC (11.9 g, 55.20 mmol) was added slowly at 25° C. It was then stirred for further 6 h. After completion of the reaction (monitored by TLC), it was passed through a short pad of silica gel (230-400 mesh) using CH$_2$Cl$_2$ as eluent. The combined organic layers were concentrated under reduced pressure to give aldehyde 4a (4.2 g) which was pure enough to be used for the next step.

Yield: 85%; gum; IR (CHCl$_3$): u$_{max}$ 667, 756, 850, 1155, 1215, 1253, 1278, 1345, 1476, 1712, 2989, 3123 cm$^{-1}$; $^1$H NMR (200 MHz, CDCl$_3$): δ 2.89 (t, J=7.3 Hz, 2H), 3.20 (t, J=7.3 Hz, 2H), 7.34-7.58 (m, 3H), 7.92 (d, J=7.9 Hz, 2H), 9.82 (s, 1H); $^{13}$C NMR (50 MHz, CDCl$_3$): 25.6, 44.4, 124.9, 127.5, 132.3, 133.1, 135.7, 199.9; Anal. Calcd for C$_9$H$_9$NO$_3$ requires: C, 60.33; H, 5.06; N, 7.82. found: C, 60.38; H, 5.11; N, 7.76%.

Example 28

(S)-1,2,3,4-Tetrahydroquinolin-3-ol (10)

Yield: 71%; gum, $[\alpha]^D_{25}$ −20.9 (c 1, CHCl$_3$); 96% ee (HPLC).

Example 29

(S)-Methyl 3-hydroxy-3,4-dihydroquinoline-1(2H)-carboxylate (11)

To a stirred solution of tetrahydroquinolin-3-ol 10 (200 mg, 1.34 mmol) and methyl chloroformate (1 mL, 13 mmol) in CH$_2$Cl$_2$H$_2$O (4:1), was added K$_2$CO$_3$ (1.8 g, 13 mmol) at 0° C. and the reaction mixture was further allowed to stir for 6 h at 25° C. Progress of reaction was monitored by TLC and after completion of reaction, a saturated solution of NH$_4$Cl (20 mL) was added. The organic layer was separated; the aqueous layer was extracted with CH$_2$Cl$_2$ (2×50 mL). Combined organic layers were washed with brine (2×25 mL), dried over anhydrous Na$_2$SO$_4$ and concentrated under reduced pressure to give the crude products. Chromatographic purification of crude product with petroleum etherethyl acetate (6:4 v/v) as eluent gave 11 (291 mg) as oily liquid.

Yield: 98%; $[\alpha]^D_{25}$+21.9 (c 1, CHCl$_3$); IR (CHCl$_3$): u$_{max}$ 1469, 1589, 1608, 1704, 3419 cm$^{-1}$, $^1$H NMR (200 MHz, CDCl$_3$): δ 2.71-2.82 (m, 2H), 3.00 (dd, J=5.3, 16.7 Hz, 1H), 3.70-3.84 (m, 5H), 4.21 (m, 1H), 7.01-7.19 (m, 3H), 7.58 (d, J=8.1 Hz, 1H); $^{13}$C NMR (50 MHz, CDCl$_3$): δ 35.9, 50.4, 53.0, 64.7, 123.8, 124.3, 126.1, 126.8, 129.4, 137.4, 155.7; ESIMS (m/z) 208 [M+H]$^+$; HRMS (ESI): calcd. for C$_{11}$H$_{13}$NO$_3$ 208.0974. found 208.0969.

Example 30

(R)-Methyl 3-azido-3,4-dihydroquinoline-1(2H)-carboxylate (12)

To a stirred solution of alcohol 11 (170 mg, 0.84 mmol) in anhydrous $CH_2Cl_2$ (16 mL) kept at 0° C. under nitrogen were successively added freshly distilled $Et_3N$ (0.4 mL, 2.5 mmol) and mesyl chloride (0.1 mL, 1.26 mmol). After stirring was continued for 45 min, $CH_2Cl_2$ (90 mL) was added to the reaction mixture, which was then washed sequentially with saturated aqueous sodium hydrogen carbonate and brine, dried with anhydrous $Na_2SO_4$, and concentrated under reduced pressure.

To a solution of this crude mesylate in anhydrous DMF (10 mL) kept at 80° C. under nitrogen was added sodium azide (0.199 g, 3.1 mmol). The resulting solution was stirred at 80° C. for 4 h. Progress of the reaction was monitored by TLC and after completion of reaction, it was extracted with EtOAc. The combined organic layers were dried over anhydrous $Na_2SO_4$ and then concentrated in vacuo. The crude product was purified by column chromatography with petroleum ether/EtOAc (9:1 v/v) to give azide 12 (181 mg) as yellow liquid.

Yield: 93%; $[\alpha]^D_{25}$ −28.2 (c 1, $CHCl_3$); IR ($CHCl_3$): $u_{max}$ 1493, 1708, 2104, 2953 $cm^{-1}$, $^1H$ NMR (200 MHz, $CDCl_3$): δ 2.80 (dd, J=6.2, 16.4 Hz, 1H), 3.08 (dd, J=6.3, 17.0 Hz, 1H), 3.68-3.82 (m, 4H), 3.92-4.03 (m, 2H), 7.04-7.20 (m, 3H), 7.62 (d, J=8.1 Hz, 1H); $^{13}C$ NMR (50 MHz, $CDCl_3$): δ 32.8, 47.6, 53.2, 55.3, 123.9, 124.4, 125.6, 126.7, 129.0, 137.4, 155.0; ESIMS (m/z) 255 $[M+Na]^+$; HRMS (ESI): calcd. for $C_{11}H_{12}N_4O_2$ 255.0858. found 255.0889.

Example 31

(R)-Methyl 3-azido-6-bromo-3,4-dihydroquinoline-1(2H)-carboxylate (13)

To a solution of azide 12 (120 mg, 0.52 mmol) in acetic acid (2 ml) were successively added anhydrous AcONa (212 mg, 1.9 mmol) and $Br_2$ (0.3 mL, 0.52 mmol). The mixture was stirred at 25° C. for 1 h and then quenched with water (30 mL). The resulting solution was extracted with $CH_2Cl_2$ (2×30 mL). The combined organic layers were dried with anhydrous $Na_2SO_4$ and concentrated in vacuo. The residue was purified over column chromatography with petroleum ether/EtOAc (9:1 v/v) to give bromo azide 13 (153 mg) as thick liquid.

Yield: 95%; $[\alpha]^D_{25}$ −14.2 (c 1, $CHCl_3$); IR ($CHCl_3$): $u_{max}$ 910, 1264, 1458, 1716, 2103 $cm^{-1}$; $^1H$ NMR (200 MHz, $CDCl_3$): δ 2.78 (dd, J=5.9, 16.8 Hz, 1H), 3.08 (dd, J=5.7, 16.8 Hz, 1H), 3.77-3.96 (m, 5H), 4.01-4.04 (m, 1H), 7.25-7.33 (m, 2H), 7.55 (d, J=8.7 Hz, 1H); $^{13}C$ NMR (50 MHz, $CDCl_3$): δ 35.7, 50.32, 53.3, 64.4, 117.0, 130.0, 124.5, 125.7, 128.9, 129.6, 132.3, 136.4, 155.1; ESIMS (m/z) 332 $[M+Na]^+$; HRMS (ESI): calcd. for $C_{11}H_{11}BrN_4O_2$ 332.9963. found 332.9998.

Example 43

(R)-Methyl 3-azido-6-bromo-8-nitro-3,4-dihydroquinoline-1(2H)-carboxylate (14)

To a solution of sodium nitrate (30 mg, 0.40 mmol) in trifluoroacetic acid (5 mL) was added bromo azide 13 (100 mg, 0.32 mmol). The resulting solution was stirred at 25° C. for 30 min and then concentrated under reduced pressure. The crude product was then dissolved in EtOAc (50 mL) and the organic portion washed sequentially with saturated aqueous sodium hydrogen carbonate (10 mL), NaOH (1 M solution, 10 mL), and water (10 mL), dried with anhydrous $Na_2SO_4$, and then concentrated under reduced pressure. It was purified by column chromatography with petroleum ether/EtOAc (6:4 v/v) to give nitro compound 14 (108 mg) as a thick liquid.

Yield: 95%; $[\alpha]^D_{25}$ +59.3 (c 1, $CHCl_3$) {lit.[33] $[\alpha]^D_{25}$ +58.4 (c 0.51, $CHCl_3$)}; IR ($CHCl_3$): $u_{max}$ 1265, 1456, 1717, 2105 $cm^{-1}$; $^1H$ NMR (200 MHz, $CDCl_3$): δ 2.86 (dd, J=5.4, 16.8 Hz, 1H), 3.08 (dd, J=5.1, 16.7 Hz, 1H), 3.64-3.80 (m, 5H), 4.09-4.16 (m, 1H), 7.51 (s, 1H); 7.91 (d, J=2.1 Hz, 1H); $^{13}C$ NMR (50 MHz, $CDCl_3$): d 32.7, 47.5, 53.2, 55.5, 117.4, 123.0, 126.5, 134.8, 135.8, 144.3, 153.4; ESIMS (m/z) 393 $[M+K]^+$; HRMS (ESI): calcd. for $C_{11}H_{10}BrN_5O_4$ 393.9553. found 393.9513. further steps for synthesis of (−)-sumanirole from 14 are known in Macé, F.; Ngo, A. N.; Pauvert, M.; Dentel, H.; Evain, M.; Collet, S.; Guingant, A. *Eur. J. Org. Chem.* 2012, 22, 4240

Example 33

(S)-Di-tert-butyl-1-(6,7-dimethoxy-1,2,3,4-tetrahydroquinolin-3-yl)hydrazine-1,2-dicarboxylate (15)

To the stirred solution of nitro hydrocinnamaldehyde 4b (1.31 g, 5.5 mmol) and ditert-butyl azodicarboxylate (1.15 g, 5.0 mmol) in $CH_3CN$ (10 mL), was added D-Proline (20 mol %) at 0° C. and allowed to stir for 3 h. After the completion of reaction as indicated by the disappearance of yellow color, was added MeOH (30 mL) and 10% Pd/C (5 wt %). The reaction mixture was then stirred at 25° C. for additional 6 h under $H_2$ atmosphere (1 atm, balloon pressure). After the completion of reaction (monitored by TLC), it was filtered through pad of celite (MeOH eluent) and the solvent evaporated under reduced pressure. Chromatographic purification of the crude product [flash silica gel (230-400 mesh) and petroleum ether:EtOAc (70:30] gave the pure 15 (1.76 g).

Yield: 83%; gum, $[\alpha]^D_{25}$ +409.1 (c 1.5, $CHCl_3$); IR (CHCl3): 1158, 1207, 1252, 1366, 1391, 1518, 1704, 2929, 2977, 3323 $cm^{-1}$; $^1H$ NMR (200 MHz, $CDCl_3$): 1.44-1.48 (m, 18H), 1.80 (brs, 1H), 2.85-3.01 (m, 2H), 3.09-3.46 (m, 2H), 3.78 (s, 3H), 3.7 (s, 3H), 4.44, 4.54 (m, 1H), 6.1 (s, 1H), 6.16 (brs, 1H), 6.50 (s, 1H); $^{13}C$ NMR (50 MHz, $CDCl_3$): 28.04, 29.45, 44.84, 50.77, 55.59, 56.49, 77.00, 80.66, 81.06, 95.97, 99.63, 111.32, 113.78, 137.38, 141.64, 148.0, 154.51, 155.856; Analysis for $C_{11}H_{15}NO_5$ requires C, 59.56; H, 7.85; N, 9.92; O, 22.67 found C, 59.52; H, 7.81; N, 9.88; O, 22.61%.

Example 34

Synthesis of (S)-di-tert-butyl-1-(6,7-dimethoxy-1-Propionyl-1,2,3,4-tetrahydroquinolin-3-yl)hydrazine-1,2-dicarboxylate (16)

To the stirred solution of tetrahydroquinolin-3-hydrazine tert-butyl ester 15 (1.5 g, 3.6 mmol) and $Et_3N$ (0.722 g, 7.2 mmol) in 25 mL of $CH_2Cl_2$, was added propionic anhydride (0.930 g, 7.2 mmol) at 25° C. Reaction mixture was then stirred for 3 h and after completion of reaction (monitored by TLC), it was washed sequentially with saturated aqueous sodium hydrogen carbonate and brine, dried with anhydrous $Na_2SO_4$, and concentrated under reduced pressure to give crude product. Chromatographic purification of crude product [silica gel (230-400 mesh) and petroleum ether:ethyl acetate (60:40)] gave amide 16 (1.56 g) in pure form.

Yield 91%: gum, $[\alpha]^D{}_{25}$ −382.6 (c 2.0, $CHCl_3$); IR ($CHCl_3$): 758, 1044, 1172, 1275, 1367, 1393, 1643, 1706, 1737, 2934, 2977, 3328 cm$^{-1}$; $^1$H NMR (200 MHz, $CDCl_3$): 1.12-1.23 (m, 3H), 1.45-1.48 (m, 18H), 1.65-1.71 (m, 2H), 2.43-2.58 (m, 2H), 2.84-3.00 (m, 2H), 3.85 (s, 6H), 4.43-4.59 (m, 1H), 6.22 (s, 1H), 6.63 (s, 1H); $^{13}$C NMR (50 MHz, $CDCl_3$): 8.94, 9.72, 27.09, 27.61, 28.11, 29.80, 55.88, 81.41, 108.47, to 111.23, 154.41; Analysis for $C_{11}H_{15}NO_5$ requires C, 60.11; H, 7.78; N, 8.76; O, 23.35 found C, 60.08; H, 7.74; N, 8.72; O, 23.31%.

Example 35

(S)-1-(3-hydrazinyl-6,7-dimethoxy-3,4-dihydroquinolin-1(2H)-yl)propan-1-one (17)

To the ice-cooled solution of 16 (1.40 g, 2.9 mmol) in dry $CH_2Cl_2$ (15 mL) was added trifluoro acetic acid (2.0 g, 17.5 mmol). Then the reaction mixture was stirred at room temperature for 12 h, after the completion of the reaction (monitored by TLC) it was quenched with saturated aqueous $NaHCO_3$ and extracted with dichloromethane (3×5 mL). The combined organic layers were washed with brine and dried over anhyd. $Na_2SO_4$ and concentrated under reduced pressure to give the crude product. Chromatographic purification [silica gel (230-400 mesh) of the crude product using methanol:ethyl acetate (5:95)] gave pure hydrazine 17 (0.736 g) as colorless solid.

Yield 90%: solid, mp 104-108° C.; $[\alpha]^D{}_{25}$ +1816.3 (c 1.1, MeOH); IR ($CHCl_3$): 749, 838, 1144, 1207, 1229, 1254, 1523, 1643, 2931, 2990, 3184, 3283 cm$^{-1}$, $^1$H NMR (200 MHz, $CDCl_3$): 1.17 (t, J=7.6 Hz, 3H), 2.17 (q, J=7.4, 15.0 Hz, 2H), 2.57 (dd, J=4.3, 15.5 Hz, 2H), 2.89 (dd, J=4.3, 16.3 Hz, 1H), 3.23-3.40 (m, 5H), 3.78 (s, 6H), 6.20 (s, 1H), 6.50 (s, 1H), 7.54 (brs, 1H); $^{13}$C NMR (50 MHz, $CDCl_3$): 9.68, 14.25, 27.72, 29.73, 42.9, 49.41, 56.30, 106.32, 111.89, 119.77, 122.02, 148.33, 149.6, 174.70; HRMS (ESI, mz): Calculated for $C_{11}H_{15}NO_5Na$ (M+Na)+ 280.1661. found 280.1664; Analysis for $C_{11}H_{15}NO_5$ requires C, 60.20; H, 7.58; N, 15.04; O, 17.18 found C, 60.15; H, 7.52; N, 15.00; O, 17.12%.

Example 36

1-[(R)-3-(Dimethylamino)-3,4-dihydro-6,7-dimethoxyquinolin-1(2H)-yl]-propan-1-one (2)

A solution of hydrazine 17 (560 mg, 2 mmol) in methanol (10 mL), and acetic acid (10 drops) was treated Raney nickel (2 g, excess) under $H_2$ (80 psig) atmosphere for 24 h. After the completion of reaction (monitored by TLC), it was passed through column packed with the celite and concentrated under reduced pressure to afford the crude amine. To the crude amine, 40% aq. solution HCHO (1 mL) and $HCO_2H$ (2 mL) were added and the resulting mixture was refluxed for 3 h. After completion of the reaction, a saturated aq. $NaHCO_3$ solution (10 mL) was added and the mixture extracted with ethyl acetate (3×20 mL). The combined organic layer was washed with brine (2×20 mL), dried over anhyd. $Na_2SO_4$, concentrated under reduced pressure. Chromatographic purification of the crude product [silica gel (230-400 mesh) and petroleum ether: ethyl acetate: triethyl amine (60:38:2) as eluent] gave pure (S)-903 (2).

Yield: 73%; mp 136° C. [lit.$^5$ 135-137° C.]; $[\alpha]^D{}_{25}$ −3.2 (c 1, EtOH) {lit. $[\alpha]^D{}_{25}$ −3.3 (c 1, EtOH)};$^5$ IR ($CHCl_3$): 760, 1049, 1211, 1511, 1647, 1743, 3018, 3450 cm$^{-1}$; $^1$H NMR (200 MHz, $CDCl_3$): δ 1.12 (t, J=7.3 Hz, 3H), 2.35 (s, 6H), 2.46 (q, J=7.3 Hz, 2H), (m, 2H), 3.23-3.54 (m, 2H), 3.82 (s, 3H), 3.83 (s, 3H), 6.64 (bs, 2H); $^{13}$C NMR (50 MHz, $CDCl_3$): δ 9.8, 27.5, 29.5, 41.3, 41.4, 55.9, 55.9, 61.4, 61.8, 108.2, 111.1, 128.6, 131.8, 146.9, 173.0; Analysis for $C_{15}H_{21}N_2O_3$ requires C, 64.96; H, 7.63; N, 10.10. found C, 64.82; H, 7.60; N, 10.27%.

The invention claimed is:

1. A process for the synthesis of a chiral 3-substituted tetrahydroquinoline of general formula 2 from a 4,5 disubstituted o-nitrohydrocinnamaldehyde of general formula 1 with high enantioselectivity (99%)

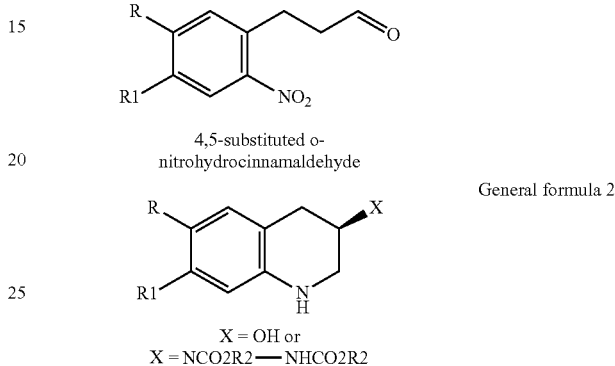

wherein, R and R1 are independently hydrogen, hydroxyl, (C1-C6) alkyl, halogen, aryl, alkylaryl, (C1-C6) alkoxy, t-Butyldiphenylsilyl ether (OTBDPS), Methoxymethyl ether (O-MOM), Tosyl, Benzyl, t-Butyl carbamate (Boc) or R and R1 together form a —O—$CH_2$—O— linkage; and X is selected from —OH or disubstituted hydrazine-1,2-dicarboxylate of formula (—N—$CO_2R_2$—NH—$CO_2R_2$); wherein $R_2$ is selected from the group consisting of branched or unbranched (C1-C6) alkyl, wherein said process comprises α-functionalizing of aldehyde by stirring the 4,5 disubstituted o-nitrohydrocinnamaldehyde, a polar aprotic organic solvent, and nitrosobenzene or dialkyl azodicarboxylate in presence of D or L proline at a temperature ranging between −20 to 30° C. for a period ranging between 10 min to 4 hrs, followed by in situ intramolecular reductive cyclization of α-functionalized aldehyde by stirring in presence of 10% Pd/C/$H_2$, (1 atm) and an organic solvent at a temperature ranging between 20° to 30° C. for a period ranging between 6 to 12 h to obtain the chiral 3-substituted tetrahydroquinoline.

2. The process according to claim 1, wherein the α-functionalization comprises α-aminooxylation of the 4,5 disubstituted o-nitrohydrocinnamaldehyde.

3. The process according to claim 1, wherein the polar aprotic solvent is selected from the group consisting of acetonitrile ($CH_3CN$), methanol (MeOH), ethanol (EtOH), chloroform ($CHCl_3$), dichloromethane ($CH_2Cl_2$), tetrahydrofuran (THF), dimethylsulfoxide (DMSO) and combinations thereof.

4. The process according to claim 1, wherein the organic solvent used in the reductive cyclization is selected from the group consisting of ethanol, methanol, propanol, isopropanol, t-butanol, pentanol, $CH_3CN$, THF, $CH_2Cl_2$ and combinations thereof.

5. The process according to claim 1, wherein the dialkyl azodicarboxylate is selected from the group consisting of diethyl azodicarboxylate, diisopropyl azodicarboxylate, di tert-butyl azodicarboxylate, dibenzyl azodicarboxylate and di 4-chlorobenzyl azodicarboxylate.

6. The process according to claim 1, wherein the D or L proline is present with concentration in the range of 10 to 20 mol %.

7. The process according to claim 1, wherein yield of the chiral 3-substituted tetrahydroquinoline is in the range of 70-87%.

8. The process according to claim 1, wherein enantiomeric excess of the chiral 3-substituted tetrahydroquinoline is in the range of 90-99%.

9. The process according to claim 1, wherein the 3-substituted tetrahydroquinoline is further converted to therapeutic agents, namely (−) sumanirole with 96% ee, and 1-[(S)-3-(dimethylamino)-3,4-dihydro-6,7-dimethoxyquinolin-1(2H) yl]propan-1-one, (S)-903 with 92% ee.

10. The process according to claim 4, wherein the organic solvent used in the reductive cyclization is methanol or a mixture of acetonitrile and methanol in the ratio of 1:3.

11. The process according to claim 1, wherein the α-functionalization comprises α-amination of the 4,5 disubstituted o-nitrohydrocinnamaldehyde.

* * * * *